United States Patent [19]

Fostick

[11] 4,041,932
[45] Aug. 16, 1977

[54] METHOD FOR MONITORING BLOOD GAS TENSION AND PH FROM OUTSIDE THE BODY

[76] Inventor: Moshe A. Fostick, 758-18th Ave., San Francisco, Calif. 94121

[21] Appl. No.: 547,649

[22] Filed: Feb. 6, 1975

[51] Int. Cl.$^2$ .............................................. A61B 5/00
[52] U.S. Cl. ................................. 128/2 G; 128/2 L; 356/39
[58] Field of Search .............. 128/2 L, 2 E, 2 A, 2 G, 128/2.1 E; 356/39, 41

[56] References Cited

U.S. PATENT DOCUMENTS

| | | | |
|---|---|---|---|
| 3,659,586 | 5/1972 | Johns et al. | 128/2 E |
| 3,795,239 | 3/1974 | Eberhard | 128/2 F |
| 3,810,460 | 5/1974 | Van Nie | 128/2 L X |
| 3,848,580 | 11/1974 | Hyden | 128/2 L X |
| 3,825,342 | 7/1974 | Lubbers et al. | 128/2 L |

OTHER PUBLICATIONS

Janssen, F. J., *Medicamundi*, vol. 17, No. 1 (1972), pp. 7–15.

*Primary Examiner*—Kyle L. Howell

[57] ABSTRACT

The concentration (and thus the partial pressure) of certain gases, such as carbon dioxide and oxygen and the pH (hydrogen ion concentration) in arterial blood are determined without the need for contacting the blood by first stripping off the top dry skin layer forming a "window" of small size. A small chamber is sealed to the skin around the window and the absorption in the chamber of electro-magnetic radiation of particular wavelengths resulting from the constituent of interest is noted as a measurement from which the concentration of that constituent in arterial blood is calculated. Specific embodiments of such electro-optical measuring chambers are described for measuring concentration of various specific constituents in arterial blood.

28 Claims, 20 Drawing Figures

$$G = \frac{I_0 I_{ref}}{I\, I_{ref_0}}$$

METHOD FOR MONITORING BLOOD GAS TENSION AND pH FROM OUTSIDE THE BODY

BACKGROUND OF THE INVENTION

This invention relates generally to a method for monitoring the concentration of certain constituents of interest in the blood of a patient, particularly the blood gases oxygen and carbon dioxide, as well as the concentration of hydrogen ions (pH).

It is important in the management of critically ill human patients that it be known how well the patient's life sustaining functions are performing. It has long been a goal to develop a technique for continuously monitoring the major functions of a patient. Some form of monitoring is considered to be essential in many circumstances, such as for a patient who is receiving intensive care or for a patient undergoing serious surgery. One major life sustaining function is pulmonary ventilation; that is, the function performed primarily by the lungs in exchanging carbon dioxide in a patient's blood for fresh oxygen from the air. Another major function is blood circulation of the patient which carries the blood's oxygen and carbon dioxide between the lungs and various portions of the body. A third major function is the patient's metabolism; that is, the ability of body cells and tissues to function. Monitoring of these major life sustaining functions permits corrective action to be taken in time to maintain life should a function be detected to be failing. The corrective action is usually taken almost without regard to the underlying disease which is causing the function to fail.

Blood circulation is satisfactorily observed by present techniques and available equipment that monitor blood pressure and pulse rate of a patient. However, satisfactory techniques are not now available for continuously observing the ventilation and metabolism functions. The attempts to satisfactorily monitor these functions date a long way back in the history of medicine. An early technique for monitoring pulmonary ventilation involved monitoring the air expelled from the patient's mouth during breathing for its carbon dioxide and oxygen content to determine if the oxygen/carbon dioxide exchange is being performed satisfactorily by the lungs and other organs. This technique is inadequate since in many critically ill patients large alveolar-arterial gradients develop due to atelectasis, arteriovenous shunting, and deterioration of the mechanical functions of the lungs. It is also awkward since it interferes with the patient's normal breathing.

Presently utilized techniques for monitoring the adequacy of pulmonary ventilation only provide for intermittent sampling and measuring of the partial pressure (concentration) of oxygen and carbon dioxide and the concentration of hydrogen ions (pH) in the blood. The level of oxygen measures the probability that a patient's tissues are receiving adequate nutrition. If there is not a sufficient oxygen level in the blood, respiratory therapy with blood transfusions or fluid replacement may be made to temporarily improve tissue oxygenation while the underlying cause for the problem is being diagnosed and treated.

The partial pressure or concentration of carbon dioxide in the blood and blood acidity as measured by concentration of hydrogen ions (pH) provides information as to the extent of the metabolic stress under which the patient's tissues are laboring. Unfavorable metabolic conditions as detected by monitoring carbon dioxide and pH can be attacked directly by respiratory therapy and intravenous fluids while the underlying disease causing the imbalance is being diagnosed and treated.

Such derangement of major life sustaining functions in a patient are corrected, at least temporarily, independently of the underlying disease which caused the condition. Once corrected, the tissues and the vascular system are better able to resume normal operation that help maintain life. Early detection of changes in blood gas and pH values is essential in order to prevent a cardiovascular catastrophe but no accurate and fast device is commercially available for continuously detecting such blood chemistry changes. Alterations in blood gas tension and pH often precede such function changes as can be detected by other existing techniques such as monitoring arterial and venous pressure, use of an electrocardiogram or electroencephalogram or by observing the outward clinical appearance of the patient.

The most straight forward approach to these blood chemistry measurements is to periodically withdraw an arterial blood sample from the patient and then test it to determine the various concentrations. This technique suffers the disadvantage of not continuously providing the desired information, requiring a significant amount of blood to be withdrawn from the critically ill patient over a period of time and further requiring manual implementation. Furthermore, the data obtained represent the blood constituent concentrations only at an instant in time and does not reflect trends. Inaccuracies of such techniques, even with elaborate testing devices, is discussed by Adams et al in *Anaestheia*, Vol. 22, No. 4, Oct., 1967, pp. 575-597. Serious complications, thrombosis and embolism, may develop in patients during and following arterial puncture or catheterization as reported by Formanek et al in *Circulation*, XLI, pp, 833-839 (1970).

There has been a great deal of effort in the past to develop an accurate, real time technique for monitoring blood gas tension and pH. A substantial amount of work has been performed by others in the direction of developing extracorporeal instruments to which the patient's circulatory system is coupled in order to provide more or less continuous analysis of blood gas tension and pH data. For example, such work has been reported by Walton et al in *Biomedical Sciences Instrumentation*, Vol. 7, pp. 155-158, and by Clark et al in *Computers and Biomedical Research*, 4, pp. 262-274 (1971).

Another approach for continuous measurement of these parameters which has received a great deal of attention in the past decade is the temporary implanting in an artery a device for detecting the concentration of one or more constituents of interest in the patient's blood. One class of such devices utilizes a gas permeable membrane at the end of a catheter that is extended into an artery with the blood gases permeating therethrough. These gases extracted from the catheter assembly by a pump without withdrawing blood. These gases are analyzed by a mass spectrometer, or some other device, substantially continuously. Such inter-arterial techniques are described in numerous papers in the technical literature, such as by Brantigan et al in the *Journal of Applied Physiology*, Vol. 28, No. 3, March 1970, pp. 375-377, and by Dardik et al in *Surgery, Gynecology and Obstetrics*, December 1970, pp. 1157-1160. Another intra-arterial technique includes the direct insertion of a miniaturized pH electrode at the tip of a catheter for the measurement of blood pH. One such device is described by Band et al in *Journal of Applied Physiology*, 22(4), 1967, pp. 854-857.

Yet another blood gas tension and pH measuring approach receiving some attention during the past decade and which overcomes the implantation disadvantage is to monitor gases passing through the skin. The content of these gases is proportional to the concentration of blood gases and the pH of blood within the patient. This approach is based upon the knowledge that blood vessels are distributed to an area just below the skin in a quantity that supplied blood in excess of the needs of the skin. The measurement of carbon dioxide and oxygen, for example, escaping through the skin from these blood vessels is an indication of the concentration and partial pressure of such constituents in the arterial blood of the patient.

One specific application of the skin gas measurement approach has been to position an inlet device of a mass spectrometer against the skin of a patient and pumping desired escaping gases therefrom for analysis. Another suggested technique, as described in U.S. Pat. No. 3,659,586 - Johns et al (1972) and by Johns et al in *Biomedical Sciences Instrumentation*, Vol. 5, 1969, pp. 119-121, teaches the use of a carbon dioxide sensor for positioning on the patient's skin over a "window" are wherein the top most dry skin layer (stratum corneum) of the epidermis has been removed, according to the method reported by Pinkus in *Journal of Investigative Dermatology*, 16, pp. 383-386 (1951) and its effects as reviewed by Tregear in *Physical Functions of Skin*, p. 21 (1966). Carbon dioxide permeates a membrane of the electrode into its interior, causing conductivity changes of a liquid therein which is measured as an indication of the carbon dioxide concentration of the blood. A similar type of skin electrode suggested to be used without stripping the skin is described in West German Pat. No. 2,145,400, and the German publication *Biomedizizische Technik*, 1973, No. G, pp. 216-221.

Despite all of the effort, as summarized above, to develop a satisfactory technique for continuous monitoring of blood gas tension and pH, no continuous real time monitoring technique is presently in commercial use. There is a very strong need for a simple, accurate and safe monitoring apparatus. However, present efforts are primarily limited to improve the accuracy of existing intra-arterial and skin electrode devices.

SUMMARY OF THE INVENTION

The strong need for an accurate, continuous and real time monitoring of blood gases and pH has been met by the technique of the present invention, which takes a different approach to the monitoring of gases through the skin than that previously taken. Briefly, the technique of the present invention includes the formation of a skin "window" in a small area of a patient by removal of substantially all of the stratum corneum (the top dry layer of the skin) in the area. Such a window is preferably less than one inch square. An enclosed chamber is positioned tightly against the skin around the window so formed and sealed thereto by sterile grease or adhesives such as the types commercially available for sealing other medical instrumentation elements to the human skin. The chamber and adjacent skin is heated to above normal skin temperature. Gases or fluids are collected in the chamber from the patient through the skin window for a time until equilibrium is reached. The internal portion of the chamber is an extension of the patient's body, at least insofar as the constituent of interest is concerned. An electromagnetic energy beam in the visible or near visible region of the spectrum is then directed through the chamber to an energy detector by beam forming and detecting devices provided by part of the chamber itself. The wavelength of the electromagnetic energy beam is selected to be highly absorbed in the chamber with increasing concentration of the constituent of interest, such as carbon dioxide or oxygen. The attenuation of the beam as it passes through the chamber is thus an indication of concentration (and thus the partial pressure) within the arterial blood of the patient.

The term "fluids" as used herein in its medical sense means biological liquids and does not refer to gases.

The transcutaneous gas tension and pH can be monitored by this technique without any effect on the patient and it has been found that the results are many times more accurate than those obtained by the approaches of others as outlined above. The skin window may be formed on the patient with sterile adhesive tape by pressing it over the area to be stripped and then removing it. This is a very insignificant modification of the human body which heals within about one week, preferably with the aid of some skin paste to prevent infection.

The improvement of the present invention has only been briefly summarized above. In the preferred embodiments described hereinafter with respect to the drawings, additional objects, advantages and aspects of the present invention are described in carrying out this novel approach. The chambers and portions of the instrumentation mounted thereon maybe as small as about 1.5 cubic inches, either including an electromagnetic energy source and detector on opposite walls of the gas or fluid collecting chamber or by fiberoptics connected therewith to a source and detector in a central instrumentation package. Carbon dioxide and oxygen are measured by a structure that includes two standardizing chambers of known concentration of the constituent of interest and additionally are provided with a mechanism for directing the detecting electromagnetic energy beam in time sequence through the two standard chambers and the chamber that has collected gases through the skin window. In this way, there is continuous calibration of the instrument with known standards. In a preferred detecting device for measuring pH, an indicator liquid is confined in the chamber with a fluid and gas permeable membrane serving as an interface between said liquid and said skin window. The indicator solution changes color in proportion to the transcutaneous pH of the patient being monitored, thus altering the transmission of the electromagnetic energy beam through the indicator solution to provide a measurement.

DESCRIPTION OF THE PREFERRED EMBODIMENTS

Figure 1:
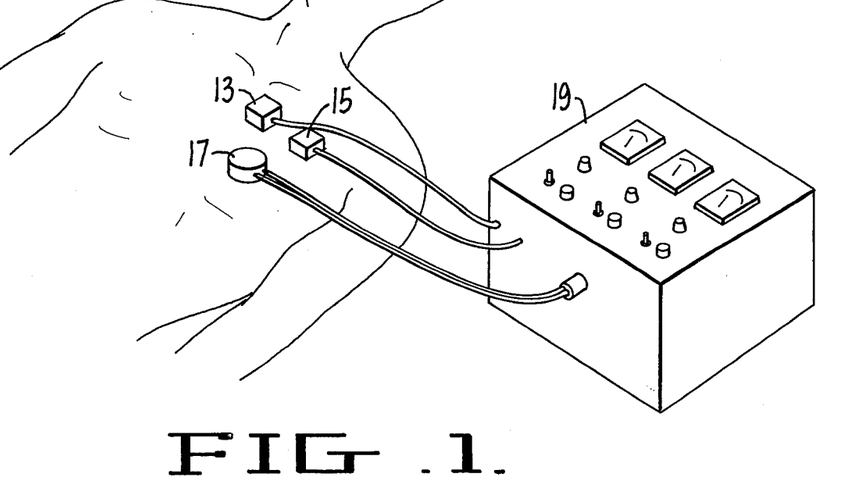
FIG. 1 illustrates generally the use of equipment that embodies the various aspects of the present invention.

Referring initially to FIG. 1, a patient 11 has three skin cells 13, 15 and 17 placed in contact with his or her skin in an appropriate location, such as the chest adjacent a shoulder, as shown. These cells are connected with an appropriate central control and display instrument 19. The instrument 19 supplies each of the cells, 13, 15 and 17 with required power and receives from the cells electrical or light signals indicative of the quantity being measured by each of the cells. These quantities can be displayed by the instrument 19 for observation by medical personnel, can be recorded on a chart recorder, etc. The cell 13, as an example, can be provided and connected for measuring the transcutaneous carbon dioxide concentration of the patient. Similarly, the cell 15 can be connected to measure the transcutaneous oxygen concentration of the patient. In addition, the cell 17 can be provided for measuring the transcutaneous pH of the patient. All of these measurements are made in real time without having to enter an artery and without having to withdraw blood from the patient.

Figure 2:
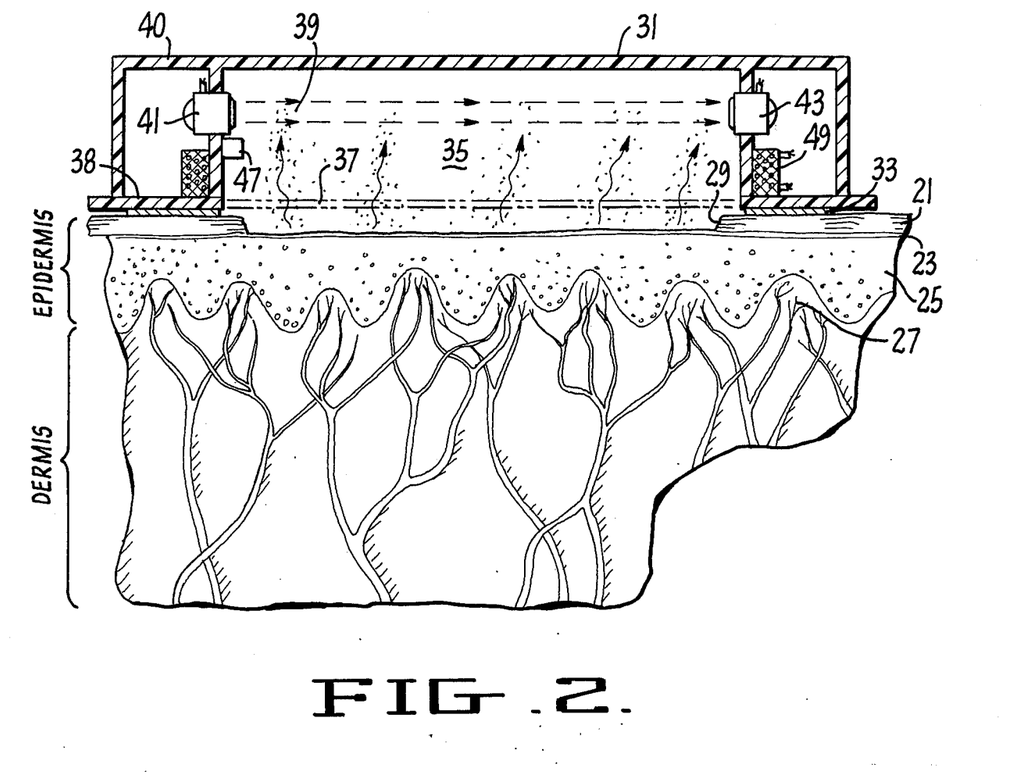
FIG. 2 illustrates in an enlarged view a crosssection of the top surface of the human skin with an instrument according to the present invention generally shown therewith.

Referring to FIG. 2, the principles of the various aspects of the present invention are generally described. The structure of the first few milimeters of the human skin is shown in an illustrative form in FIG. 2. The top epidermis layer includes a top most stratum corneum layer 21. The next layer into the skin is the stratum lucidum 23. Beneath these two layers within the epidermis is the stratum granulosum and stratum germinativum, indicated collectively in FIG. 2 as 25. Beneath the epidermis layer is the dermis skin layer which includes a large number of blood vessels, such as those indicated at 27, near its top most surface. Certain of these surface blood vessels are connected with arteries further beneath the surface of the skin and others are connected with blood veins further into the skin. As an indication of the scale of FIG. 2, a typical human epidermis has a thickness within the range of from 60 microns to 100 microns over the entire body, except for the palms of hands or the soles of feet wherein the stratum corneum is often 600 microns thick by itself.

The various aspects of the present invention are carried out by first removing the top portion of the epidermis skin layer, principally the dry crusty stratum corneum layer 21 (FIG. 2). The removal of such a portion forms a "window" 29. The principal resistance of the skin to diffusion of gases and fluids therethrough is presented by the stratum corneum layer 21. Therefore, removal of an area thereof to form the window 29 gives access into the patient through the skin. A cell 31 is attached to the skin around the window 29 by a standard adhesive layer 33. The cell 31 is open to the side facing the window 29 but is otherwise enclosed to form a chamber 35 that is a physiological extension of the human body. The excessive amount of blood vessels in the top of the dermis layer of the skin equilibrates the blood gases, hydrogen ions, electrolytes, and other solutes with the skin's tissue fluids. Gases or fluids then permeate transcutaneously through the epidermis below the window 29 and into the chamber 35 of the skin cell 31 and equilibrate with the cell's contents. The transcutaneous concentration of a constituent of interest that indicates the concentration within arterial blood of the patient is then determined by measuring the concentration within the cell 35 of that constituent directly or of one related to it.

The skin window 29, in order to give an order of magnitude in size, will usually be less than one inch maximum dimension. The stratum corneum 21 is removed to form the window 29 by any of several methods, the most convenient being the use of adhesive tape that is pressed against the skin in the area 29 and then removed. Removal of the adhesive tape also removes the stratum corneum layer 21. The window 29 can also be formed, alternatively, by a controlled mechanical excision or abrasion of the epidermis layer, either with or without first being chemically fixed in situ. Another technique is the application of keratolytic pharmaceutical to the skin surface as a paste, cream or liquid in the area where the window is desired to be. Fluid and gas diffusion through this skin into the chamber 35 then occurs. After the testing is completed, the stratum corneum layer 21 will again form in the window area 29 within a day or so and is preferably aided in its healing by the use of a medical cream.

In carrying out the various aspects of the present invention, the chamber 35 can be opened without restriction to the skin or, alternatively, may utilize a structure 37 thereacross, such as in the form of a membrane, in order to selectively permit passage of gases or fluids into the chamber 35. Additionally, the structure 37 may include a perforated, mechanically rigid structure for preventing volume changes in the chamber 35 from skin deformation that may result from patient movement during measurement. A beam 39 of visible or near-visible electromagnetic radiation is directed across the chamber 35 from the source 41 in one wall of the chamber 35 to a detector 43 in an opposite wall. The radiation beam 39 has its wavelength ranges chosen to include a region that is highly absorbed by a blood constituent of interest, such as carbon dioxide or oxygen. For detecting the concentration of carbon dioxide in the cell, radiation within the far infrared region of the spectrum is used. For detecting oxygen, wavelengths within the ultra-violet range are used.

For measurement of transcutaneous pH the fluids and gases entering the chamber 35 from within the patient's skin are not observed directly but rather the membrane 37 is utilized and contains a liquid indicator dye within the chamber 35, such as a phenol red solution. One of several visible light wavelengths is then passed through the indicator dye. Radiation absorbance therein is proportional to the transcutaneous pH of the patient.

Such photometric measurements are generally temperature sensitive so the skin cell of FIG. 2 is provided with an electrical heating unit 45 as part thereof as well as a temperature sensing element 47. An appropriate electrical controller, such as would be positioned in the control unit 19 of FIG. 1, is provided to operate in response to the temperature sensing element 47 to drive the heater 45 in the manner to maintain the temperature of the chamber 35 at a constant level. It is usually preferred to maintain this temperature above normal body temperature by a comfortable amount.

A feature common to all embodiments of this invention is that the light absorbance measurement is made right in the chamber that contacts the skin. No gases or fluids are removed from this chamber for analysis elsewhere. The gases or fluids being photometrically examined remain in the chamber 35 which extends only an inch or so from the patient's skin. Certainly there is no need to have such gases and fluids extended more than 6 inches from the skin, and they usually remain even closer to the patient's skin during analysis. Only electrical wires and/or optical fiber bundles need extend from the skin cell of FIG. 2 to a central control, this makes increased accuracy possible.

A base flange 38 of the embodiment of FIG. 2 is made to have an extended area that is at least as great as the area of the opening into the chamber 35 from the skin, and preferably greater. This large area spreads the weight of the cell out over the patient's skin away from the window area to reduce a pressure that can occlude blood flow in superficial vessels under the removed skin area. In any event, a cover 40 is preferably employed to enclose and optically isolate the cell completely.

The various aspects of the present invention have been generally described with respect to FIG. 2. More specific embodiments of skin cells for the particular measurements of carbon dioxide and oxygen concentration levels in blood, and blood pH levels, are separately described with respect to the following FIGS. 3–16.

Referring to FIGS. 3–6 a particular skin cell having a principal utility of measuring the transcutaneous carbon dioxide concentration is described. A casing 51 houses the miniaturized electro-optical system of the skin cell of FIG. 3–6. A set of electrical conductors 53 communicates between this cell and the central control unit 19. A chamber 55 is formed by cell 51 that is pressed against the skin 59 and sealed by sterile adhesive or grease 61 about a skin window 63 that has been formed on the patient in a manner described previously with respect to FIG. 2. The chamber 55 may contain a disposable plastic member 57 which transmits the infrared radiation used to measure carbon dioxide. The disposable plastic part 57 may be pre-sterilized and used for only one patient, thus avoiding the necessity to sterilize the skin cell instrument itself between different patients. The plastic member 57 includes a base plastic sheet with a cube like shape being formed in one area thereof, resulting in the chamber 55 having an unobstructed opening through the base sheet while being otherwise enclosed. The plastic member 57 may include a flat rigid screen at the interfacing plane of chamber 55 and the skin to prevent volume changes caused by bulging of the skin into the chamber and to improve thermal conductivity between the cell and the skin. A gas permeable fluid impermeable membrane may be affixed to the screen or affixed alone in the interfacing plane of the skin and the cell.

Figure 3:
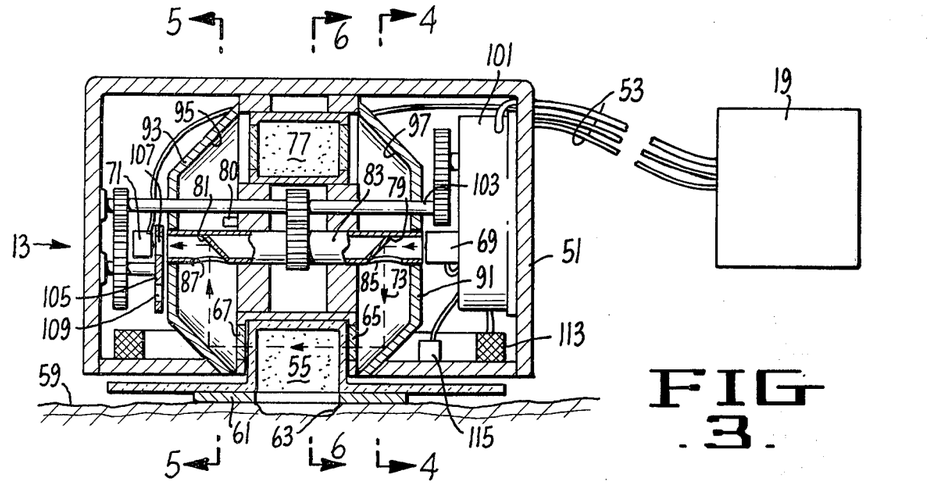
FIG. 3 is a cross-sectional view of one embodiment of the invention.
Figure 4:
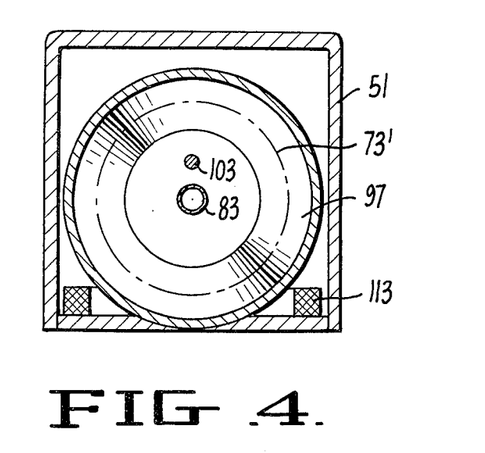
FIG. 4 is a sectional view of the apparatus of FIG. 3 taken across section 4—4 thereof.
Figure 5:
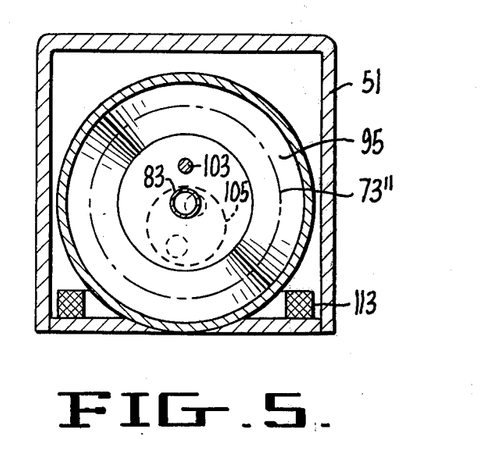
FIG. 5 is a sectional view of the apparatus of FIG. 3 taken across section 5—5 thereof.
Figure 6:
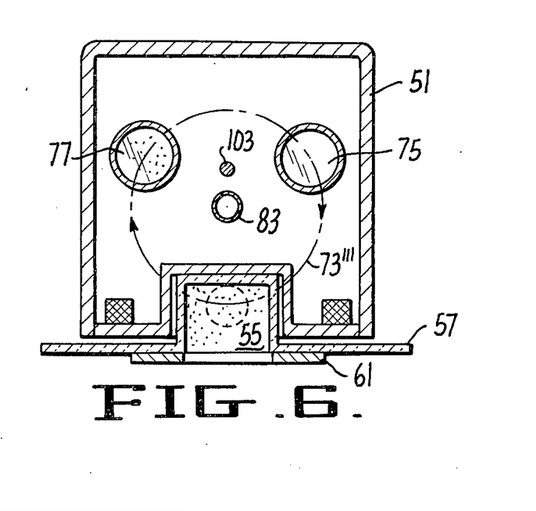
FIG. 6 is a sectional view of the apparatus of FIG. 3 taken across section 6—6 thereof.

The skin cell housing 51 is provided with an indentation to receive the rectilinear portion of the plastic member 57 that forms the chamber 55, this indentation including light transparent windows 65 and 67 on opposite sides thereof. A radiation source 69 is provided within the casing 51 and energized externally through the cable 53. A detector 71 of such radiation is also provided within the casing 51 with the electrical output of the detector being connected through the cables 53 from the skin cell. A radiation beam 73 formed by the light source 69 is alternately scanned through the sample chamber 55, and two standard gas chambers 75 and 77 that each contain a known concentration of carbon dioxide.

The optical system within the casing 51 includes two planar mirrors 79 and 81 that are fixedly attached to a tubular member 83 at opposite ends thereof at angles to change the direction of the radiation beam 73 by 90°. The tubular member 83 is opened at its opposite ends adjacent the source 69 and detector 71 and additionally has circular openings 85 and 87 in the sides thereof for the passage of the radiation beam 73 therethrough. The tubular member 83 is held axially aligned between the source 69 and the detector 71 by being journaled within interior wall sections 91 and 93.

Opposing mirror surfaces 95 and 97 are provided on the inside surfaces of internal wall structures 91 and 93, respectively. These mirror surfaces 95 and 97 are portions of similarly shaped cones having their vortices coincident with the axis of rotation of the tubular member 83, said axis passing through the middle of the source 69 and detector 71. Thus, the beam 73 from the radiation source 69 is first directed to the mirror 79, thence at a right angle to the mirror 97 which redirects the beam in another right angle across to the mirror 95. The mirror 95 again bends the beam 73 in a right angle to strike the mirror 81. The mirror 81 redirects the beam 73 in another right angle onto the detector 71. Thus, as the tubular member 83 is rotated, the radiation beam 73 is scanned over the mirror 97 in a path 73' (FIG. 4) and also in a path 73" of the mirror 95 (FIG. 5) where such light transmission between the mirrors 95 and 97 is not blocked. Such radiation transmission is blocked by opaque surfaces, however, between the mirrors 95 and 97 except in the regions of the sample cell 55 and the reference cells 75 and 77. The reference cells 75 and 77 are provided with appropriate radiation transmission windows for passage of the beam 73 therethrough for interaction with the gaseous mixture held therein. A position sensor 80 gives a signal of the rotation position of the tube 83 and thus tells which cell is being measured.

An electric motor 101 is provided within the casing 51 and by an appropriate gearing arrangement provides rotary motion to a shaft 103 that is positioned parallel to the tube 83 and similarly held journaled in the interior wall portions 91 and 93. By an appropriate gearing relationship, the uniform velocity rotation of the shaft 103 is applied to the tubular member 83. Also driven by the shaft 103 is a filter wheel 105 having radiation filters 107 and 109 in different positions thereon. The speed of the filter wheel 105 is calculated so that each of the filter regions 107 and 109 thereof are passed in front of the detector 71 while the beam 73 is scanning through each of the sample chamber 55 and reference cells 75 and 77. That is, the absorbance by the gases in each of the chambers 55, 75 and 77 is measured by passing the radiation beam 73 therethrough.

This measurement is taken for each chamber at two different narrow bandpass ranges. For carbon dioxide, one of the filters is designed to pass radiation in the far infrared at 4.3 microns (43,000 Angstroms) in wavelength, a wavelength that is highly absorbed by the presence of carbon dioxide. As a reference, the other of the filters 107 and 109 is designed to pass radiation in the far infrared at 4.1 microns (41,000 Angstroms), a wavelength which is not absorbed significantly by carbon dioxide. The light transmission measurements so made by the mechanism of FIGS. 3-6 of each of the three chambers 55, 75 and 77 at each of these two different wavelengths thus gives six pieces of information from which the concentration of carbon dioxide in the patient's arterial blood may be manually or electronically calculated and displayed.

Figure 8:
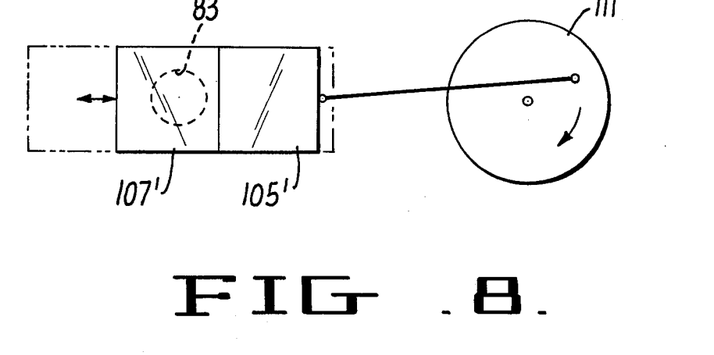
FIG. 8 shows an alternate concentration of a portion of the instrument illustrated in FIGS. 3-6.

An alternative filter structure is shown in FIG. 8 wherein two bandpass filters 105' and 107' are provided immediately adjacent one another in a structure that is alternatively slid back and forth relative to the rotating tube 83 and the detector 71. This linear motion is provided by an eccentric attached to a wheel 111, the wheel 111 being driven from the shaft 103. Any filter mechanism may be used that accomplishes the goal of examining each of the gases in the chambers 55, 75 and 77 in alternating sequence for light absorption at each of two wavelengths, one which is highly absorbed by the presence of carbon dioxide therein and another wavelength that is substantially unaffected by the presence of carbon dioxide therein.

Referring briefly again to FIG. 3, a heating element 113 is provided within the casing 51. A temperature sensor 115 is also provided to give an electrical signal proportional to the temperature within the casing 51. Appropriate thermostatic control may then be provided external of the casing 51 to maintain it and the chambers 55, 75 and 77 at a uniform temperature above the temperature of the partient's skin.

The electrical current output of the detector 71 gives the information from which the concentration of carbon dioxide in the cell is determined. It is this current value under six specific conditions that is used in making this carbon dioxide concentration determination. These six current quantities are as follows:

$i_{01}$ - the detector current when the light beam 73 is passing through the standard cell 75 (provided with no carbon dioxide) at the wavelength absorbed by carbon dioxide.

$i_{R1}$ - the detector current when the radiation beam 73 is passing through the standard cell 77 (provided with approximately 10% carbon dioxide) at the wavelength absorbed by carbon dioxide.

$i_{S1}$ - the detector current when the radiation beam 73 is passing through the sample cell 55, also at the wavelength that is highly absorbed by carbon dioxide.

$i_{02}$, $i_{R2}$, $i_{S2}$ - are, respectively, counterparts of the above three current quantities except they are taken at the radiation wavelength that is not absorbed by carbon dioxide.

Figure 7:
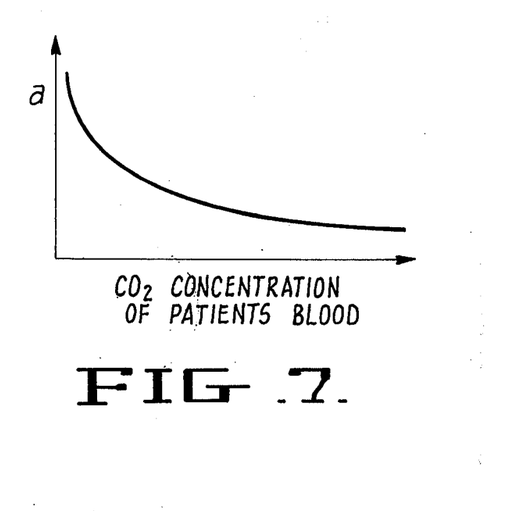
FIG. 7 illustrates the relationship between the quantity measured by the instrument of FIGS 3-6 and a concentration level that is desired to be determined.

Referring to FIG. 7, the carbon dioxide concentration of the cell is determined from an empirically formed curved from a constant $a$ that is calculated from the six current quantities identified above, according to the following relationship:

$$a = \frac{\frac{i_{01} - i_{S1}}{i_{01} - i_{R1}}}{\frac{i_{02} - i_{S2}}{i_{02} - i_{R2}}} \tag{1}$$

The curve of FIG. 7 is plotted for a given cell instrument and system by taking measurements while positioning the cell over atmospheres whose carbon dioxide level is known. The quantity $a$ is thus calculated from the current readings obtained by the cell structure of FIGS. 4-6 for a number of different carbon dioxide concentration levels of known value. Once the curve of FIG. 7 is plotted, the cell structure is able to be employed in the manner intended to determine in real time the unknown carbon dioxide concentration level of the critically ill patient. The quantity $a$ may be manually calculated and applied to a curve of the FIG. 7 type, or all of this may be done by analog or digital calculator apparatus within the control unit 19.

It will be noted that the numerator of equation (1) above will change with the carbon dioxide level within the sample chamber 55 since all of the quantities in the numerator are dependent upon the radiation absorbance at the wavelength (4.3 microns in this specific example) at which carbon dioxide is highly absorptive. The denominator of equation (1) above is determined from the current readings at non-absorptive wavelengths (4.1 microns in this specific example). The denominator will thus vary only with changing optical conditions and thus serves to compensate for such changing conditions that affect the readings in the numerator of equation (1) at the highly absorptive wavelengths. Such changing conditions can be changing radiation source and detector sensitivities, for example. Also, patients may use different sterilized plastic members 57 and the radiation absorptive characteristics of this member could vary from time to time. The technique outlined above eliminates these variations as affecting the results obtained.

Figure 9:
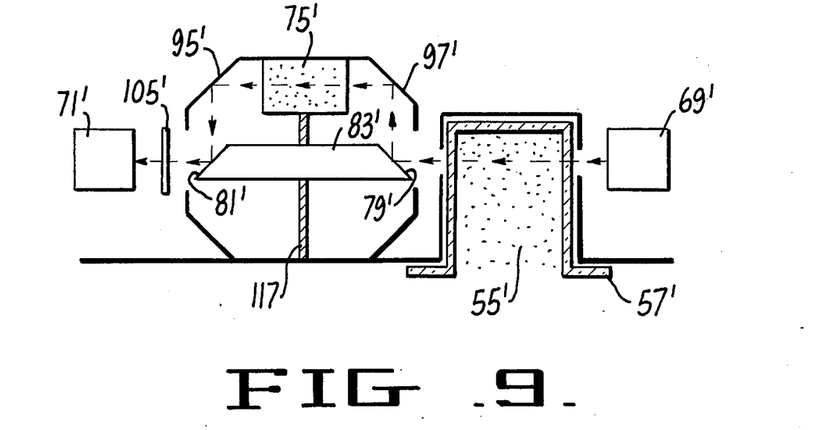
FIG. 9 schematically illustrates another embodiment of the invention that is a partial rearrangement of components of the embodiment illustrated in FIGS. 3-6.

A less accurate but often satisfactory variation of this technique is illustrated with respect to FIG. 9 wherein only one radiation wavelength is utilized, that wavelength that is highly absorbed by the carbon dioxide (4.3 microns in this specific example). The filter 105' of FIG. 9 is thus designed to pass 4.3 microns. The remaining elements of FIG. 9 having counterparts in the embodiments of FIGS. 3-6 are shown with the same reference numeral and a prime (') added.

In FIG. 9, all of the radiation output of the source 69' passes through the sample chamber 55'. The rotating optical system in the modification of FIG. 9 alternately passes the radiation output from the chamber 55' through reference cells 75' and 77' or cuts off the radiation completely by a provision of an opaque wall 117. The current output of the detector 71' thus has three values of interest which are used in calculating the desired carbon dioxide concentration in the skin cell:

$i_D$ — is the current output of the detector 71' when the path of the light beam is blocked by the wall 117; that is, when no radiation from the source 69' is incident upon the detector 71';

$i_{S+R}$ — this is the current output of the detector 71' when the radiation is passed through the sample chamber 55' and the standard chamber 77' having a 10% concentration of carbon dioxide;

$i_{S+O}$ — is the current output of the detector 71' when the radiation passes in series through the sample chamber 55' and the standard chamber 75' having no carbon dioxide content. A quantity a which is related to the concentration of the skin cell in the same manner as described previously with respect to FIG. 7, is given by the following expression:

$$a' = \frac{i_D - i_{S+R}}{i_D - i_{S+O}} \qquad (2)$$

A curve such as that described with respect to FIG. 7 may also be generated with known carbon dioxide concentration levels for the modified instrument of FIG. 9. It will be noted that in the modification of FIG. 9 that the plastic 57' is common to all readings and thus variations in the absorbance of different plastic members is automatically taken care of. This simplicity is obtained from the embodiment of FIGS. 3-6 at the cost of some error in the readings of the standard absorbance by the gases in the standard cell 75' and 77' but this error has been found to be unimportant in achieving accuracy within present clinical tolerances.

Figure 10:
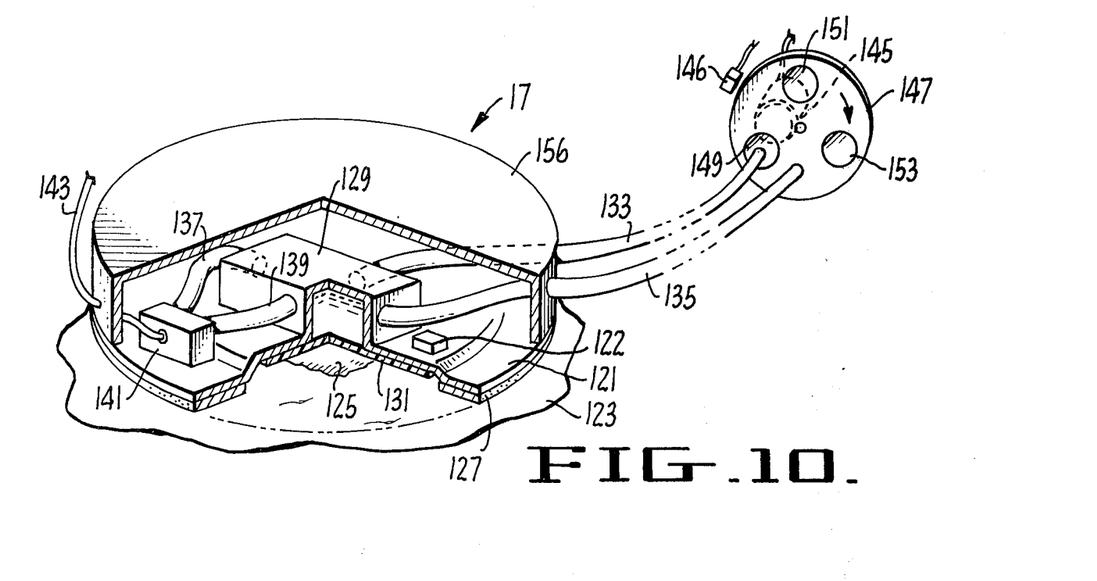
FIG. 10 shows a cut away view of another embodiment of the invention.

Referring to FIG. 10, the cell 17 for determining the pH level of a liquid which equilibrates with the patient's tissue fluids and blood is illustrated. A bottom plate 121 of this cell is placed against a patient's skin 123 about a window 125 formed therein in the manner described above with respect to FIG. 2. The cell 17 is sealed to the patient's skin by a sterile adhesive layer 127. The bottom plate 121 of the cell of FIG. 10 is formed into a rectangular chamber 129 having an opening downward but otherwise being sealed. The downward opening of the chamber formed by the structure 129 is sealed with a dialysis membrane 131, such as one made of a cuprophane material. The closed chamber 129 is filled with a buffered phenol red solution and in use is positioned over the skin window 125. Gases, hydrogen ions, and electrolytes escaping through the skin window 125 thus enter the chamber 129 through the membrane 131 and react with the phenol red solution to give various changing light absorbance characteristics proportional to the pH level of the tissue fluids and blood of the patient being monitored.

In the particular embodiment of the pH cell of FIG. 10, two separate bundles of light transmitting fibers 133 and 135 supply light through the walls of adjacent sides of the chamber 129. The other two walls of the chamber 129 are fitted with additional optical fiber bundles 137 and 139 that join together at a single light detector 141. An electrical output of the light detector 141 is carried to the external instrumentation by conductors 143. It is the total of the light carried by the fiber bundles 137 and 139 that is detected by the detector 141. The bundle 137 receives light transmitted in the long direction of the chamber 129 from the light bundle 135. The light bundle 139, on the other hand, received the light propagated within the chamber 129 across its short dimension by the source light fiber bundle 133.

The source ends of the fiber bundles 133 and 135 are given incident light from a source 145 through a color filter wheel 147. The filter wheel 147 contains one each of a green, blue and red filter. A blue filter 149 is designed to pass a narrow light band about 4,300 Angstroms (433 nm). A green filter 151 is designed to pass a narrow light band about 5,600 Angstroms (560 nm). Each of these blue and green wavelengths are variably absorbed by the phenol red solution in the chamber 129 depending upon the pH level of the patient being monitored. A red filter 153 is optically provided on the color wheel 147 to provide a reference wavelength that is absorbed the same amount regardless of the pH level of the patient's blood. This red reference wavelength may be 6,500 Angstroms (650 nm). The reference wavelength is desirable to permit elimination of absorbance of the green and blue wavelengths that is caused by factors other than the pH level, such as neutral density changes. It will be noted from FIG. 10 that each of the optical bundles 133 and 135 is alternately illuminated with each of the three colors. Only one of these fiber bundles is illuminated at a time, their ends being spaced so that while a filter is in front of one of the optical fiber bundles 133 or 135 the other is positioned in a non-illuminated portion of the wheel 147. Thus, the detector 141 receives six distinct signals of interest, one for each of the three colors and for each of the long and short dimensions of the cell 129. A position detector 146 gives a signal that indicates the rotatable position of the color wheel 147, a signal which is used to identify the various detector signals.

Figure 13:
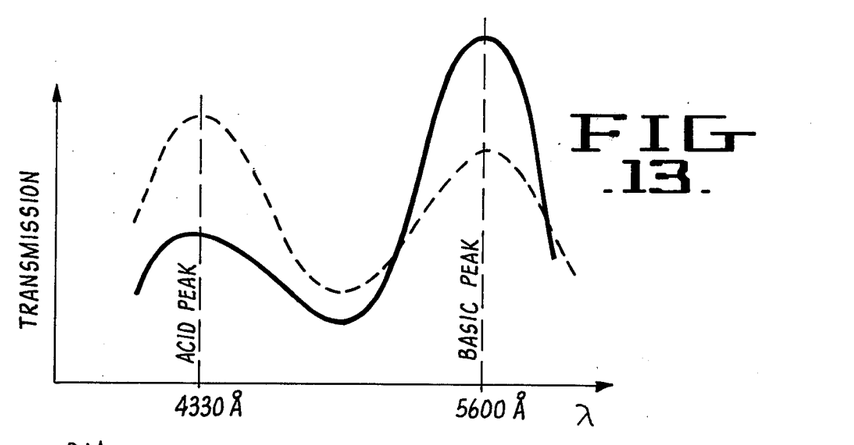
FIG. 13 includes light absorbance curves for the embodiment of FIGS. 10 through 12.
Figures 14, 15:
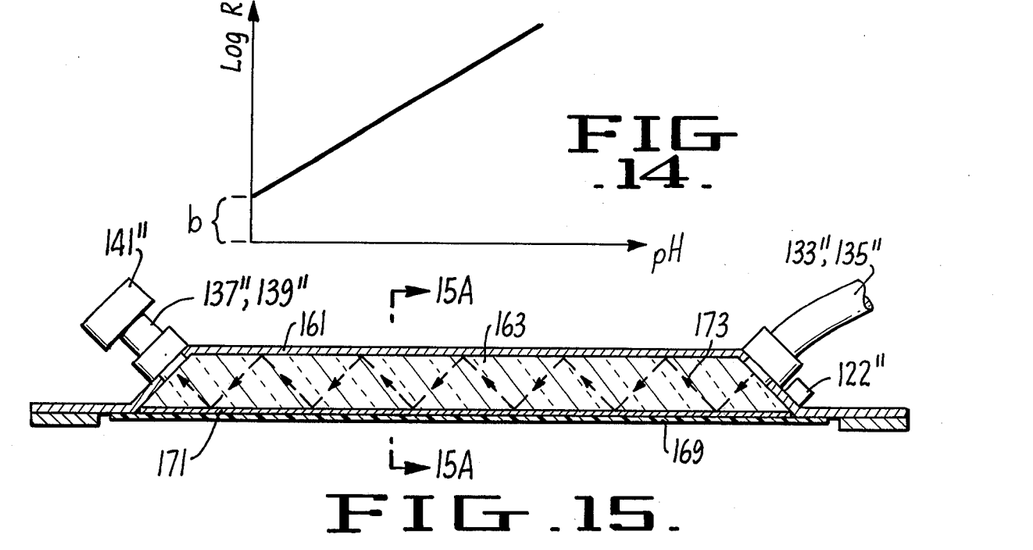
FIG. 14 is a graph illustrating the operation of the embodiments of FIGS. 10-12.
FIG. 15 is another modification of the instrument embodiment of FIGS. 11 and 12.
Figure 15A:
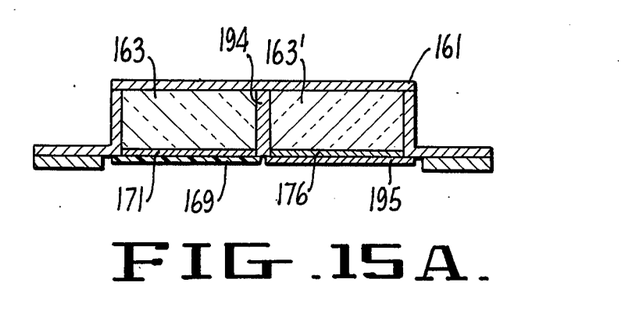
FIG. 15A is a view of the embodiment of FIG. 15 taken at section 15A—15A thereof.

The manner in which these signals are utilized to give a reading of the patient's blood pH level may be explained with respect to FIGS. 13 and 14. Referring initially to FIG. 14, a straight line curve gives the relationship between pH and a quantity "log R" which may be expressed by the following equation:

$$pH = c \, \log R + b \qquad (3)$$

A constant c is the slope of the curve of FIG. 14. This and the intercept constant b will remain the same for any given cell, once it is calibrated. The quantity log R varies as a function of the blood pH level of the various patient's to which the calibrated cell may be applied. The quantity R denotes the acid indicator concentration divided by the basic indicator concentration. For the cell of FIG. 10, the factor R is given as follows:

$$R = \frac{I_{Blue-S} - I_{Blue-L}}{I_{Gn-S} - I_{Gn-L}} \qquad (4)$$

Where $I_{Blue-S}$ is the blue light intensity received across the short dimension of the chamber 129, $I_{Blue-L}$ across the long dimension, $I_{Gn-S}$ is the green light intensity received across the short dimension, and $I_{Gn-L}$ across the long.

FIG. 13 shows the variable light absorbance of the phenol red solution within the chamber 129 for different pH levels. The solid curve of FIG. 13 shows the amount of light transmitted through the phenol red at the blue "acid peak" wavelength of 4,330 Angstroms. Similarly, the green "basic peak" at 5,600 Angstroms is indicated. At a lower pH level, such as indicated by the dashed line of FIg. 13, the relationship between the light transmission (or conversely light absorbance) changes, thus affecting the quantity log R of equation (3) above as illustrated in the curve of FIG. 14. The measuring of the light absorbance in the chamber 129 of FIG. 10 is both the long and short directions and the use of these four signals as indicated in equation (4) above to determine the pH is compensating for optical changes that may occur over time, such as light source and detector changes and transmission characteristics of the fiber optics.

A better correction is achieved by adding the third red wavelength. $K_{blue}$, $K_{green}$ and R are calculated in the following manner:

$$R = \frac{(I_{blue\ S} - I_{blue\ L}) K_{blue}}{(I_{green\ S} - I_{green\ L}) K_{green}} \tag{5}$$

Where $$K_{blue} = K_{0\ blue} \times \frac{K_{red}}{K_{0\ red}}$$

$$K_{green} = K_{0\ green} \times \frac{K_{red}}{K_{0\ red}}$$

$K_O\ red = I_o\ red\ L - I_O\ red\ S$
$K_O\ blue = {}_o\ blue\ L - I_o\ blue\ S$
$K_O\ green = I_o\ green\ L - I_o\ green\ S$ These prior three values are determined with chamber 129 filled with water prior to calibration and are stored in a calculating section of box 19. $K_{red}$ is measured continuously, and equals $I_{red}\ L - I_{red\ S}$.

The configuration of FIG. 10 makes it unnecessary to have a separate reference cell. However, if a separate reference cell is desired, the configuration of FIGS. 11 and 12 may be used for a pH cell. Similar illuminating optics are employed with the embodiment of FIGS. 11 and 12 as have previously been described with respect to FIG. 10. The illuminating light bundle 133' (corresponding to 133 of FIG. 10) illuminates a reference cell 155 that is filled with a phenol red solution or a chemical or a filter, with absorption in the three wavelengths. The sample cell 157 is open to the skin by a membrane 131' while the reference cell 155 is not so opened. The light transmittance of the sample cell at the blue and green wavelengths discussed above will vary with respect to that of the reference cell 155 at the transcutaneous pH level of a patient being monitored so changes. Fiber bundles 137' and 139' collect the light at the opposite ends of both the reference and sample cells 155 and 157 and join together at a single light detector 141'. The cells 155 and 157 are light tight to prevent cross-talk between them. The cover 156' has a function of keeping the interior of the cell isolated from ambient light.

Figures 11, 12:
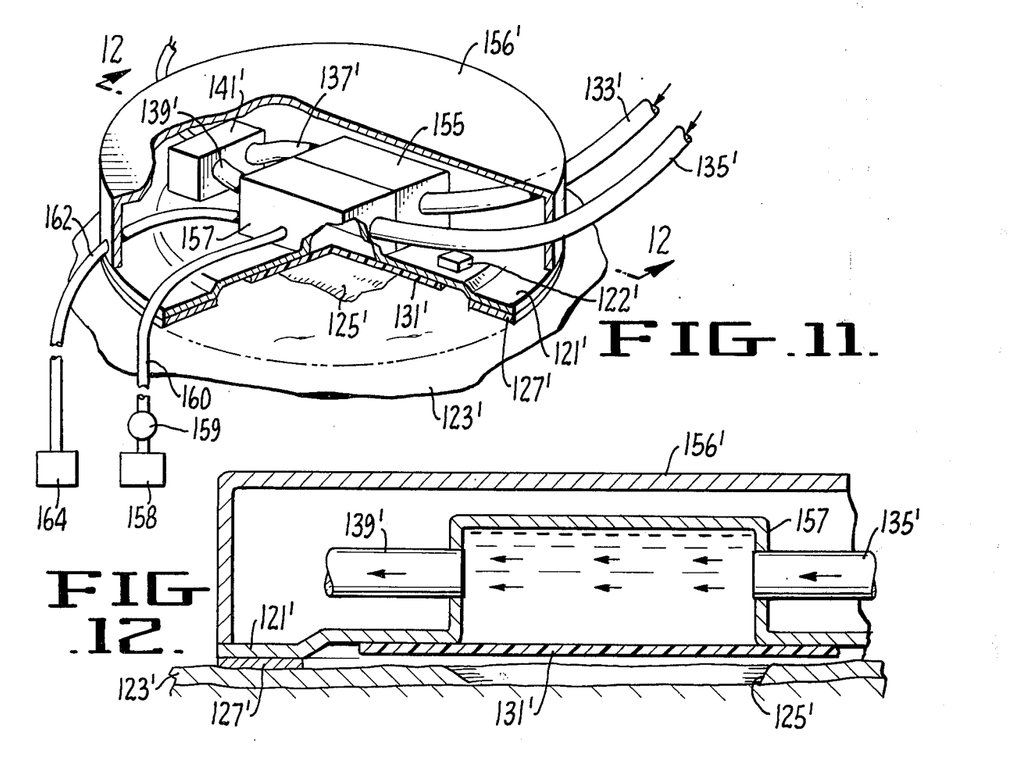
FIG. 11 shows yet another embodiment of the invention that is a modification of the embodiment of FIG. 10.
FIG. 12 is a cross-sectional view of the instrument of FIG. 11 taken across section 12-12 thereof.

In the embodiments of FIGS. 10-12 which use an indicator solution, certain irreversible changes may take place in the sample cell during a single test. A refreshing of the liquid indicator solution in the sample cell is thus desirable in many circumstances. Referring to FIG. 11, a fresh indicator solution reservoir 158 and liquid pump 159 are shown schematically. The pump 159 pushes through a flexible liquid tube 160 fresh indicator solution into the chamber 157. The used solution is thus pushed out through another flexible liquid carrying tube 162 into an equilibrated liquid reservoir 164. This liquid refreshing can, where desired take place after each pH test made with such cells.

For the embodiment of FIGS. 11 and 12, the factor R of equation (3) and FIG. 14 is given by the following:

$$R = \frac{\frac{I_{Blue-R}}{I_{Blue-S}}}{\frac{I_{Gn-R}}{I_{Gn-S}}} \tag{6}$$

Where $I_{Blue-R}$ is the blue light intensity received through the reference cell 155, $I_{Blue-S}$ is the blue light intensity received through the sample cell 157, $I_{Gn-R}$ is the green light intensity received through the reference cell 155 and $I_{Gn-S}$ is the green light intensity received through the sample cell 157.

Each of the cells of the embodiments of FIG. 10 and FIGS. 11 and 12 are provided with appropriate covers, heaters and thermostates in order to maintain them at a uniform temperature above the temperature of the patient's skin under investigation.

As with the carbon dioxide cells previously described, the pH detecting cells of FIG. 10 and FIGS. 11 and 12 are calibrated by application to solutions with known pH levels in order to determine the constants c and b of equation (3) above for that cell. Once these are determined, the cell is ready for pH measurement of the critically ill patient.

To further correct for absorption changes not caused by pH changes the third red wavelength is used. R and correction factors $K_{Blue}$ and $K_{Green}$ are calculated in the following manner:

$$R = \frac{\frac{I_{Blue-S}}{I_{Blue-R}} \times K_{blue}}{\frac{I_{Green-S}}{I_{Green-R}} \times K_{green}} \tag{7}$$

Where $$K_{blue} = K_{0\ blue} \times \frac{K_{red}}{K_{0\ red}}$$

$$K_{green} = K_{0\ green} \times \frac{K_{red}}{K_{0\ red}}$$

$K_{red}$ equals the continuous value of $\frac{I_{red\ S}}{I_{red\ R}}$ $$K_{0\ red} = \frac{I_{0\ red\ S}}{I_{0\ red\ R}}$$

$$K_{0\ blue} = \frac{I_{0\ blue\ S}}{I_{0\ blue\ R}}$$

$$K_{0\ green} = \frac{I_{0\ green\ S}}{I_{0\ green\ R}}$$

These prior three values are measured prior to calibration with sample chamber filled with water. Values of $K_{O\ red}$, $K_{O\ blue}$ and $K_{O\ green}$ are stored in a calculating part of box 19.

Referring to FIG. 15, yet another modification of a pH cell is illustrated. In the cross-sectional view of FIG. 15, a cell housing 161 is filled with two glass plates 163 and 163+ of high optical quality and are optically isolated by a partition 194. The illuminating light bundle 133'' (corresponding to 133 of FIG. 10) illuminates the reference plate 163' that is separated from the outside by a sealing plate 195. The optional gap 176 between the glass plate 163' and the sealing plate 195 may be filled with dye or other chemicals and together serve as a reference cell. The sample cell is formed by a plate 163 and a membrane 169 that is provided on its bottom side. A layer 171 of dye fills the gap between the plate 163 and the membrane 169 or is chemically bound to the bottom side of the plate 163. The light fiber bundle 135'' (corresponding to the bundle 135 of FIG. 10) illuminates the sample cell. A short fiber bundle 137'' collects the light from the opposite side of the reference cell (plate 163') and fiber bundle 139''' collects the light from the opposite side of the sample cell (plate 163). Both bundles join together at a single light detector 141''. The light from the optical bundles 133'' and 135'' travel in paths indicated by the ray 173 reflecting back and forth within the glass plate 163' and 163 from their opposite surfaces. In such a travel light, the light strikes the dye later 171 and the reference layer 176 a large number of times. The intensity of light that is gathered by the output optical bundle 139" depends upon the absorbing of the layers 171 and 195 or 176. The indicator dye in the layer 171 changes its light absorbance properties in response to the acidity of the fluids traveling through the membrane 169 and which thus indicates the transcutaneous pH level of a patient being monitored. The dye layer 171 is preferably made of phenol red. pH is calculated in the manner of equations (6) or (7) above.

The variation of the pH cell shown in FIG. 15 is, in practice, constructed similarly to the embodiment of the cell of FIGS. 11 and 12. That is, there is a sample cell as shown in FIG. 15 with a membrane through which the skin's fluids and gases can travel and there will also be a similar cell to the one described with respect to FIG. 15 for a reference, the reference cell having no interaction with the patient being monitored. The optical system, including filter wheel, detector, etc., would be the same as that described with respect to the embodiment of FIGS. 11 and 12. A principal advantage of the variation described with respect to FIG. 15 is the very compact small physical size that such a pH cell can take and with its smaller volume of dye it provides a faster time response to pH changes. In addition to what has been described with respect to FIG. 15, as with all of the other embodiments of skin cells described herein, it is desirable that the pH cell have a heat source and a temperature controlling system to maintain the temperature uniform at a level above the skin temperature. An ultrasonic source 122, 122' and 122''' in FIGS. 10, 11 and 15, respectively, serve to improve liquid mixing within the sample chamber 129.

Figure 16:
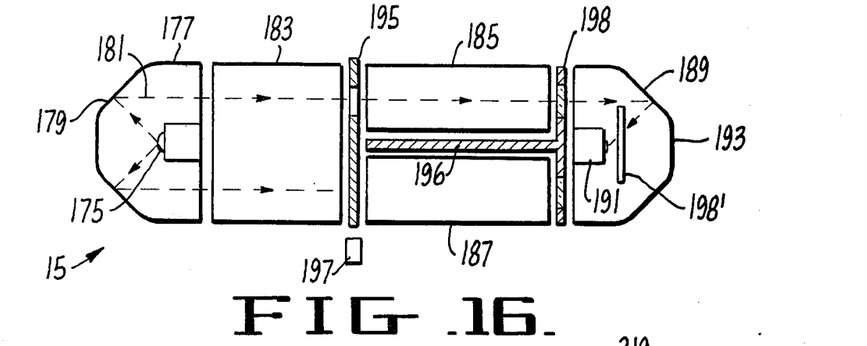
FIG. 16 shows yet another embodiment of the present invention.

Referring to FIG. 16, an embodiment of a self contained skin cell for measuring the transcutaneous oxygen level of a patient is schematically illustrated. Many of the principals and apparatus for carrying out the oxygen concentration method is the same as the previously described carbon dioxide technique. A principal difference is, however, that free space between optical components is not allowed for measuring oxygen concentration. Thus, the cell of FIGS. 3–6, 8 and 9 described for carbon dioxide measurements have to be altered to eliminate the space between optical components. This space is undesirable because the air that fills it affects the results of the oxygen concentration tests. Ultra-violet wavelengths, preferably 1,450 Angstroms or 1,850 Angstroms, are used for making the oxygen measurement. Atmospheric air is also absorptive at these wavelengths so is undesirable in the path of radiation.

The system schematically illustrated in FIG. 16 shows space between the optical components for ease of illustration but its design is such that this space can be and is in practice eliminated by tightly fitting the various components together. A source 175 of light is sealed in an appropriate structure 177. One end 179 of that structure is a mirror shaped to receive the radiation from the source 175 and to redirect it in a substantially columnated beam 181 out of a substantially transparent other end of the structure 177. The light beam 181 next passes through an optical gas chamber 183 and thence through parallel sample and reference gas containing cells 185 and 187, each one optically isolated. The light after passing through these cells passes through an optical filter 198 and enters an appropriate enclosed detector structure 189 containing sealed therein a detector 191 with a focusing mirror element 193 to direct the total energy output of the gas cells 185 and 187 onto the detector 191. As an alternative, option filter 198 is replaced by filter 198' that is positioned in front of the detector 191. A mechanical chopped 195 is disposed between the units 183 and 185, 187 to alternately blank out light through one of the cells 185 and 187. The detector 191 thus alternately receives light from the sample cell 185 and then from the reference cell 187 and given an electrical output accordingly. An electronic position sensor 197 associated with the rotating chopped 195 also gives a signal as to which of the cells 185 or 187 is being illuminated and detected at the moment.

The sample cell 185 communicates with a skin window of a patient in a manner described above. The reference cell 187 contains a gaseous mixture of known oxygen concentration, for instance 10%. The detector 191 also receives, for a portion of its cycle, no light whatsoever and this dark reading is of use to determine the amount of current reading from the detector that is due to factors other than light incidence upon it.

From the three detector current readings in the cell of FIG. 16 (light intensity through the sample cell 185, $i_S$; light intensity through the reference cell 187, $i_R$; and the detector current when no light is incident upon it, $i_D$) can be used to calculate a quantity $a'''$ as follows:

$$a''' = \frac{i_D - i_R}{i_D - i_S} \tag{8}$$

The quantity $a'''$ can give, from a graph similar to the type discussed with respect to FIG. 7, the oxygen concentration of the sample cell. Such a graph is made by taking several readings while positioning the cell over atmospheres with known oxygen concentrations, thus calibrating the cell of FIG. 16 before its use.

The oxygen detecting cell of FIG. 16 can be modified to add a third cell, this being a reference cell having no oxygen whatsoever, in a manner described earlier with respect to the carbon dioxide cell of FIGS. 3–6. A quantity $a''''$ proportional to the oxygen concentration in the sample cell is thus given as follows:

$$a'''' = \frac{i_O - i_S}{i_O - i_R} \tag{9}$$

Where $i_O$ is the detector output when this third zero concentration cell is utilized.

The chamber 183 is a negative filter that may optically be employed. The chamber 183, when used, is filled with nitrogen ($N_2$) to remove the frequencies from the light beam 181 before they strike the sample and reference cells that are affected by the presence of nitrogen. Other more standard light filters may also be employed in the optical path. Also, other optical arrangements for deriving multiple beams for multiple sample and reference cells from a single source may be employed, the same technique being used to recombine the beams after passing through these cells onto a single detector. This type of cell discussed with respect to FIG. 16 is also adaptable for carbon dioxide measurements as discussed above.

As with all of the carbon dioxide cells described herein, it is desirable that the oxygen sample chamber corresponding to the carbon dioxide sample chamber 55 in FIG. 3 will have a screen at its interfacing plane with the skin with an optional gas permeable fluid impermeable membrane. The oxygen cell will also have a heat source and a temperature controlling system.

Figures 17, 17A, 17B:
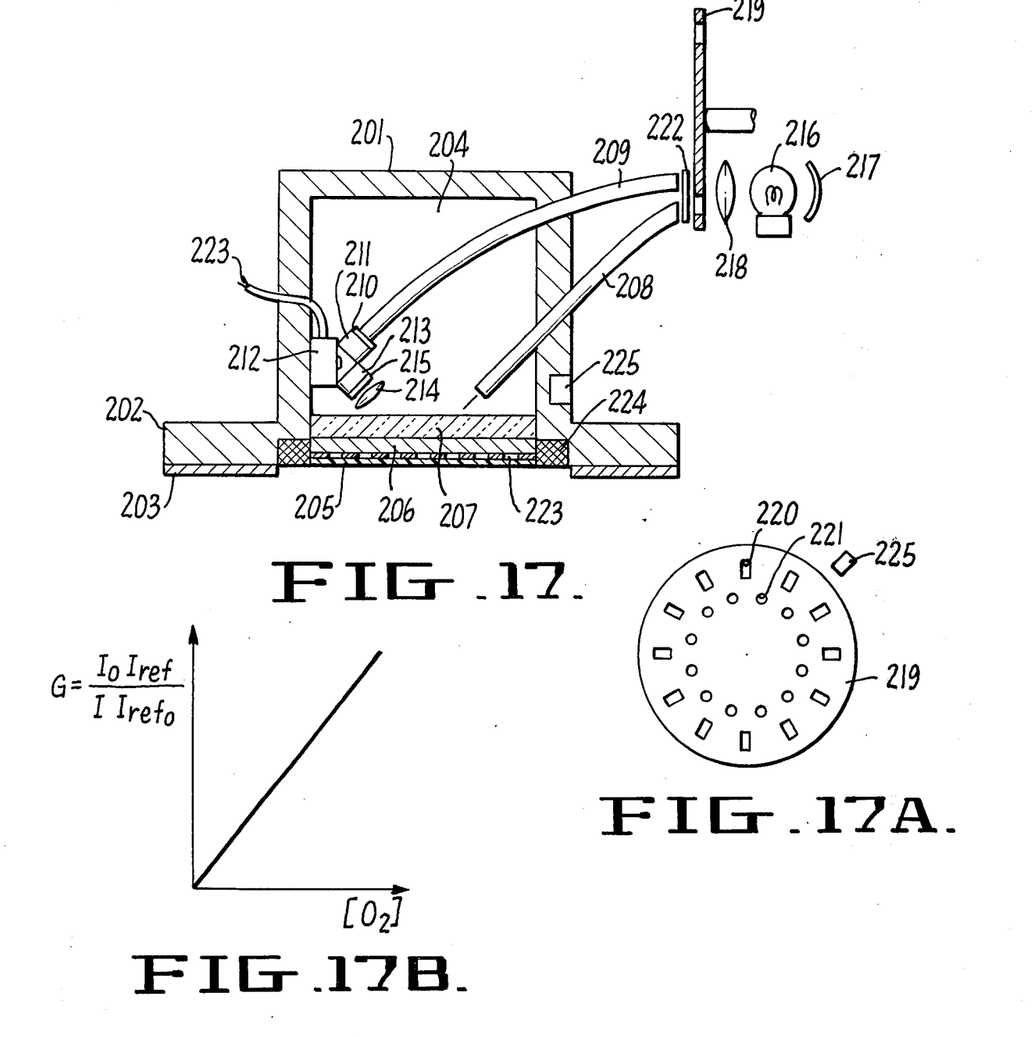
FIG. 17 shows a further embodiment for measuring oxygen concentration.

Another technique for determining transcutaneous oxygen concentration is illustrated with respect to FIG. 17. In this embodiment, the phenomenon of luninescence quenching is utilized. This phenomenon is described generally in a book by Parker entitled *Photoluminescence of Solutions*, pages 493–496 (1968).

A bottom plate 202 of a cell is placed against the patient's skin by a sterile adhesive-sealant layer 203. The casing 201 with the plate 202 of the cell of FIG. 17 form a chamber 204 having an opening downward but otherwise being sealed and light tight. A gas permeable liquid impermeable membrane 205 is provided on the bottom side of the cell with an optional screen 223. A thin layer 206 of fluorescent compound such as pyrenebutyric acid in solution of the right viscosity, such as the mineral oil glycerol, fills the space between the membrane 205 and an ultra-violet transparent optical plate 207. In a modification of this method, the fluoroescent compound of layer 206 can be chemically bound to the bottom surface of the plate 207 or to the upper surface of the membrane 205 which faces the plate 207.

The chemical layer 206 is characterized by emitting radiation of certain wavelengths when excited by ultraviolet radiation, the intensity of the emitted radiation depending inversely upon oxygen content within the layer 206. This oxygen content depends upon the oxygen concentration of the patient's body that permeates through the membrane 205.

In the particular embodiment of the oxygen cell of FIG. 17 an optical fiber bundle 208 serves to transmit light which illuminates the film of the fluoroescent compound 206 and excites its fluorescence. A second optical fiber bundle 209 transmits reference light through an optional light attenuator 210 to one arm of a bifurcating light pipe 211 which transmits the light to a photodetector 212. The direct reference measurement of the source corrects for excitation intensity changes.

The other arm 213 of the bifurcated light pipe receives the fluorescent light through an optional light collecting optics 214 and through a filter 215 to the photodetector 212. The filter 215 is designed to pass light in the fluorescence band of the chemical compound of layer 206, such as 3700–4300 Angstroms (370–430 nm) for pyrenebutyric acid.

The source end of the fiber bundles 208 and 209 are given light from a source 216 with its light concentrating mirror 217 and optics 218. The light passes through a filter wheel 219 (FIGS. 17 and 17A) which has two concentric circles of apertures on alternating radii. The larger apertures on the outer circle 220 pass light to illuminate the source end of the fiber bundle 208 through the filter 222. The smaller apertures on the inner circle 221 pass light to illuminate the source end of the fiber bundle 209 through the filter 222. The filter 222 is designed to pass light in the excitation band of the fluorescent compound in layer 206, such as 3000–3500 Angstroms (300–350 nm) for pyrenebutyric acid. Only one of the fiber bundles is illuminated at a time, their ends being spaced so that while an aperture is in front of one of the optical fiber bundles 208 or 209 the other is positioned in a non-illuminated portion of the wheel 219. Thus, the detector 212 receives two distinct signals of interest, one for the direct reference beam through the fiber bundle 209 and one for the fluorescent light through elements 214, 215 and 216 of the optical system. Position indicator 225 provides a signal of the position of wheel 219 with respect to fiber bundles 208 and 209.

The concentration of the transcutaneous oxygen is calculated in the following manner:

$$\frac{I_o}{I} = 1 + \tau Kq[O_2]$$

is the basic expression for the relationship between the measured fluorescent intensity I in the presence of oxygen at concentration $[O_2]$ where $I_0$ is the fluorescent intensity in the absence of oxygen, $\tau$ is the fluorescence lifetime of the fluorescent compound in the absence of oxygen and Kg is the bimolecular rate constant for quenching the fluorescent compound after it was excited, by the quenching molecule such as oxygen. The corrected ratio $$G = \frac{I_o}{I} \cdot \frac{I\,\text{ref}}{I\,\text{ref}_o}$$

where I ref is the measured source intensity and $I\,\text{ref}_0$ is the measured source intensity during calibration. Values $I_0$ and $I\,\text{ref}_0$ are stored in a calculating section of box 19.

During calibration, the oxygen cell 201 is exposed to a number of different known oxygen concentrations and the value of the ratio G is plotted producing the curve of FIG. 17B.

Once the curve is plotted, the cell structure is able to be employed in the manner intended to determine in real time the unknown oxygen level of the critically ill patient. The value of the ratio G may be manually calculated and applied to a curve similar to that of FIG. 17B, or all of this may be done by analog or digital calculator apparatus within the control unit 19.

As with all of the other embodiments described herein, a heater 224 and temperature sensor 225 are provided to maintain the temperature of the entire cell at something in excess of the patient's skin temperature.

Although the techniques of the present invention have been described with respect to a preferred embodiment thereof, it will be understood that the invention is entitled to protection within the full scope of the appended claims.

I claim:
1. A method of monitoring a concentration of a constituent of interest in tissue fluids or blood of a person, comprising the steps of:
 removing a substantial amount of the person's stratum corneium skin layer over an area,
 positioning a chamber over said area in a manner to permit gases or fluids escaping from the body through said area to enter the chamber,
 sealing the chamber to the skin around said removed skin area in a gas and liquid tight manner, thereby to isolate the chamber and the removed skin area from surrounding atmosphere,
 collecting in the chamber gases or fluids emitted from the removed skin area in the chamber for a time until the transfer of the constituent of interest between the chamber and the body of the person is in equilibrium, passing a beam of electromagnetic energy above the skin through the collected gases or fluids within said chamber, said electromagnetic energy including certain wavelengths that are absorbed an amount proportional to the concentration of said constituent of interest in said chamber, and measuring the energy absorption of said certain wavelengths of said electromagnetic beam passing through said chamber, whereby the absorption level is proportional to the concentration of a constituent of interest in the body of said person.

2. The method according to claim 1 which comprises the additional step of heating said chamber during the measurement to maintain it at a uniform temperature in excess of the temperature of the patient's skin.

3. The method according to claim 1 wherein the fluids within said chamber are maintained within 6 inches of the patient's skin during the step of measuring the energy absorption.

4. The method according to claim 1 wherein the step of passing a beam includes positioning a source of electromagnetic energy in a side wall of said chamber, said source being energized by electrical wires leading to said chamber, and further wherein the step of measuring the energy absorption includes the positioning of an electromagnetic energy detector on a side wall of said chamber opposite the wall of said electromagnetic energy source, the signal of said detector being communicated externally by electrical conductors connected therewith.

5. The method according to claim 1 wherein the step of passing a beam includes generating the electromagnetic energy a distance away from said chamber and communicating it to said chamber by an optical fiber bundle that terminates in one side wall of said chamber, said step of measuring the energy absorption including positioning a detector a distance from said chamber with another optical fiber bundle communicating between said detector and a side wall of said chamber that is opposite the side wall in which the source fiber bundle terminates.

6. The method according to claim 1 wherein the step of positioning a chamber includes positioning an opening of the chamber over the removed skin area in a manner that gases can be transferred between the person and said chamber without any physical barrier whatsoever therebetween.

7. The method according to claim 1 wherein the step of positioning chamber includes orienting an opening of the chamber across said removed skin area and further includes the positioning of a membrane across the chamber opening, said membrane being selective to permit gases of fluids of interest to pass therethrough while excluding particles not of interest.

8. The method according to claim 7 wherein said chamber is filled with a liquid whose light absorbance qualities change in proportion to the amount of a constituent of interest that passes through said membrane into the chamber.

9. The method according to claim 8 wherein said liquid is a phenol red solution, whereby the light transmittance therethrough is proportional to the blood pH of said person.

10. The method according to claim 9 wherein the step of passing the beam includes passing narrow bandwidth ranges of light in each of the blue and green portions of the spectrum through said chamber.

11. The method according to claim 1 wherein said step of passing a beam comprises including radiation wavelengths in the far infrared that are highly absorbed by carbon dioxide, whereby the measured absorption level is proportional to the amount of carbon dioxide in the body of said person.

12. The method according to claim 1 wherein said step of passing a beam comprises the inclusion of certain ultraviolet radiation wavelengths that are highly absorbed by oxygen, whereby said absorption measurement gives a measurement of the concentration of oxygen in the body of said person.

13. The method of monitoring a concentration of a constituent of interest in tissue fluids or blood of a person, comprising the steps of:

removing a substantial amount of the person's stratum corneum skin layer over an area, positioning a chamber over said area in a manner to permit gases or fluids escaping from the body through said area to enter the chamber, said positioning step including orienting an opening of the chamber across said removed skin area, and further includes the step of positioning a rigid perforated structure across said opening, whereby the person's skin is prevented from bulging into the chamber during measurement, sealing the chamber to the skin around said removed skin area in a gas and liquid tight manner, thereby to isolate the chamber and the removed skin area from surrounding atmosphere, collecting gases or fluids emitted from the removed skin area in the chamber for a time until the transfer of the constituent of interest between the chamber and the body of the person is in equilibrium, passing a beam of electromagnetic energy through said chamber, said electromagnetic energy including certain wavelengths that are absorbed an amount proportional to the concentration of said constituent of interest in said chamber, and measuring the energy absorption of said certain wavelength of said electromagnetic beam passing through said chamber, whereby the absorption level is proportional to the concentration of a constituent of interest in the body of said person.

14. The method of monitoring a concentration of a constituent of interest in tissue fluids or blood or a person, comprising the steps of:

removing a substantial amount of the person's stratum corneum skin layer over an area, positioning a chamber over said area in a manner to permit gases or fluids escaping from the body through said area to enter the chamber, said positioning step including the step of supporting weight of the chamber by the skin of the person in an area surrounding said removed skin area, said supporting skin area being at least as large as the removed skin area, whereby pressure on superficial blood vessels below the removed skin area is reduced, sealing the chamber to the skin around said removed skin area in a gas and liquid tight manner, thereby to isolate the chamber and the removed skin area from surrounding atmosphere, collecting gases or fluids emitted from the removed skin area in the chamber for a time until the transfer of the constituent of interest between the chamber and the body of the person is in equilibrium, passing a beam of electromagnetic energy through said chamber, said electromagnetic energy including certain wavelengths that are absorbed an amount proportional to the concentration of said constituent of interest in said chamber, and measuring the energy absorption of said certain wavelengths of said electromagnetic beam passing through said chamber, whereby the absorption level is proportional to the concentration of a constituent of interest in the body of said person.

15. A method of monitoring a concentration of a gaseous constituent of interest in the body of a person, comprising the steps of:

removing a substantial amount of the person's stratum corneum skin layer over an area, positioning a chamber over said area in a manner to permit gases or fluids escaping from the body through said area to enter the chamber, sealing the chamber to the skin around said removed skin area in a gas and liquid tight manner, thereby to isolate the chamber and the removed skin area from surrounding atmosphere, collecting gases or fluids emitted from the removed skin area in the chamber for a time until the transfer of the constituent of interest between the chamber and the body of the person is in equilibrium, positioning a source of radiation beam adjacent said chamber, said radiation beam including a first range of wavelengths that are absorbed an amount proportional to the concentration of said constituent of interest and a second range of wavelengths that are substantially unabsorbed by the constituent of interest, positioning a radiation detector in the path of said radiation beam after passing through the gases or fluids within said chamber, said detector emitting an electrical signal proportional to the intensity of radiation incident on it, providing at least one reference material having known radiation absorbance characteristics at said first and second range of wavelengths, alternately directing said radiation beam through said chamber and said at least one reference material in turn and thence onto said detector, and monitoring the electrical signal output of said detector at each of said first and second range of wavelengths for the radiation beam after passing through the chamber and at least one reference material in turn, thereby developing at least four electrical signals which indicate the concentration of said gaseous constituent of interest in the body of a person.

16. The method according to claim 15 wherein the step of directing said electromagnetic energy beam through at least one reference material includes the step of passing the beam through a reference cell that contains a known concentration of the constituent of interest.

17. A method of monitoring a concentration of a gaseous constituent of interest in the body of a person, comprising the steps of:

removing a substantial amount of the person's stratum corneum skin layer over an area, positioning a chamber over said area in a manner to permit gases or fluids escaping from the body through said area to enter the chamber, sealing the chamber to the skin around said removed skin area in a gas and liquid tight manner, thereby to isolate the chamber and the removed skin area from surrounding atmosphere, collecting gases or fluids emitting from the removed skin area in the chamber for a time until the transfer of the constituent of interest between the chamber and the body of the person is in equilibrium, passing a beam of electromagnetic energy through said chamber, thereby to form a sample modulated beam, said illuminating electromagnetic energy including certain wavelengths that are absorbed an amount proportional to the concentration of said constituent of interest in said chamber, providing reference material having known radiation absorbance characteristics to said certain electromagnetic energy wavelengths, and alternately directing said sample modulated beam through said at least one reference material onto a radiation detector and blocking the radiation from reaching the detector, thereby developing at least two distinct detector output electrical signals which indicate the concentration of said gaseous constituent of interest in the blood of a person.

18. The method according to claim 17 wherein the step of directing said electromagnetic energy beam through at least one reference material includes the step of passing the beam through a reference cell that contains a known concentration of the constituent of interest.

19. A method of monitoring a concentration of a constituent of interest in the body of a person, comprising the steps of:

removing a substantial amount of the person's stratum corneum skin layer over an area, positioning a rectangularly shaped chamber over said area in a manner to permit gases or fluids escaping from the body through said area to enter the chamber, said chamber having a significantly longer dimension in one direction along said skin than in its orthogonal direction, sealing the chamber to the skin said removed skin area in a gas and liquid tight manner, thereby to isolate the chamber and the removed skin area from surrounding atmosphere, collecting gases or fluids emitted from the removed skin area in the chamber for a time until the transfer of the constituent of interest between the chamber and the body of the person is in equilibrium, passing two beams of electromagnetic energy through said chamber, one beam across its short dimensions and the other beam across its long dimension, said electromagnetic energy including certain wavelengths that are absorbed an amount proportional to the concentration of said constituent of interest in said chamber, separately detecting the radiation intensity of each of the two beams after they have been passed through said chamber, and combining electrical signals proportional to the detected intensity of the radiation of each of the two beams after passing through said chamber in order to indicate the concentration of a constituent of interest in the body of a person.

20. The method according to claim 19 wherein the step of positioning a rectangularly shaped chamber includes positioning a rectangularly shaped opening thereof over the removed skin area, and further includes the additional steps of closing said opening with a thin membrane and filling the enclosed chamber with a liquid phenol red solution, the step of passing two beams of electromagnetic energy through the chamber including the passing of a narrow bandwidth of wavelengths within each of the two beams within the green and blue region of the spectrum, whereby the combined electrical signals indicate the pH level in the blood of said person.

21. A method of monitoring a concentration of a constitutent of interest in tissue fluids or blood of a person, comprising the steps of:
- removing a substantial amount of the person's stratum corneum skin layer over an area,
- positioning an opening of a chamber over said area in a manner to permit gases or fluids escaping from the body through said area to enter the chamber,
- positioning a membrane across the chamber opening, said membrane being selective to permit gases or fluids of interest to pass therethrough while excluding particles not of interest,
- including in said chamber a luminescent solution characterized by emitting, in response to a certain intensity of excitation radiation in a first wavelength range, electromagnetic radiation in a second wavelength range with an intensity depending upon the concentration of the constituent of interest therein,
- sealing the chamber to the skin around said removed skin area in a gas and liquid tight manner, thereby to isolate the chamber and the removed skin area from surrounding atmosphere,
- collecting gases or fluids emitted from the removed skin area through the membrane into the chamber for a time until the transfer of the constitutent of interest between the luminescent solution and the body of the person is in equilibrium,
- directing a beam of electromagnetic energy of said first wavelength range into said chamber and onto said luminescent solution,
- measuring the intensity of electromagnetic radiation in the second wavelength range that is emitted from the luminescent solution, whereby said intensity is proportional to the concentration of a constituent of interest in the body of the person.

22. The method according to claim 21 wherein said luminescent solution includes pyrenebutiric acid and the incident radiation first wavelength range is within the ultra-violet range of the spectrum, whereby the constituent of interest being measured is oxygen.

23. A method of monitoring a concentration of a constitutent of interest in tissue fluids or blood of a person, comprising the steps of:
- removing a substantial amount of the person's stratum corneum skin layer over an area,
- positioning a chamber over said area in a manner to permit gases or fluids escaping from the body through said area to enter the chamber,
- sealing the chamber to the skin around said removed skin area in a gas and liquid tight manner, thereby to isolate the chamber and the removed skin area from surrounding atmosphere,
- collecting gases or fluids emitted from the removed skin area into the chamber for a time until the transfer of a constituent of interest between the luminescent solution and the body of the person is in equilibrium,
- passing a beam of electromagnetic energy above the skin through the collected gases or fluids within said chamber, said electromagnetic energy including certain wavelengths that are absorbed an amount proportional to the concentration of said constituent of interest in said chamber,
- alternately directing said electromagnetic energy beam through at least one reference material having set characteristics of absorption of said certain electromagnetic energy wavelengths independent of the constituent concentration in said chamber,
- measuring the intensity of the beam at said certain wavelengths at the output of said chamber and at the output of said reference material, and
- determining the concentration of the constituent of interest in the body of said person from the relative beam intensity at said outputs.

24. The method according to claim 23 wherein the step of directing said electromagnetic energy beam through reference material includes the step of passing the beam through a reference cell that contains a known concentration of the constituent of interest.

25. The method according to claim 23 wherein the fluids within said chamber are maintained within six inches of the patient's skin during the step of measuring the energy absorption.

26. The method according to claim 23 wherein the step of positioning a chamber includes positioning an opening of the chamber over the removed skin area in a manner that gases can be transferred between the person and said chamber without any physical barrier whatsoever therebetween.

27. The method according to claim 23 wherein said step of passing a beam comprises including radiation wavelengths in the far infrared that are highly absorbed by carbon dioxide, whereby the measured absorption level is proportional to the amount of carbon dioxide in the body of said person.

28. The method according to claim 23 wherein said step of passing a beam comprises the inclusion of certain ultraviolet radiation wavelengths that are highly absorbed by oxygen, whereby said absorption measurement gives a measurement of the concentration of oxygen in the body of said person.

* * * * *